US011220964B2

(12) United States Patent
Willer et al.

(10) Patent No.: US 11,220,964 B2
(45) Date of Patent: Jan. 11, 2022

(54) PORTABLE GENERATOR INCLUDING PROXIMITY SENSOR (71) Applicant: Briggs & Stratton LLC, Wauwatosa, WI (US)

(72) Inventors: Mark Willer, Brookfield, WI (US); Ryan Janscha, Brookfield, WI (US); Brandon Nigh, Elm Grove, WI (US); Austin Baeten, De Pere, WI (US)

(73) Assignee: Briggs & Stratton, LLC, Wauwatosa, WI (US)

( * ) Notice: Subject to any disclaimer, the term of this patent is extended or adjusted under 35 U.S.C. 154(b) by 83 days.

(21) Appl. No.: 16/567,925

(22) Filed: Sep. 11, 2019

(65) Prior Publication Data
US 2020/0083828 A1 Mar. 12, 2020

Related U.S. Application Data (60) Provisional application No. 62/730,352, filed on Sep. 12, 2018.

(51) Int. Cl.
*F02D 29/06* (2006.01)
*H02P 9/08* (2006.01)
(Continued)

(52) U.S. Cl.
CPC ............ *F02D 29/06* (2013.01); *F02B 63/047* (2013.01); *F02B 77/08* (2013.01); *F02D 41/22* (2013.01);
(Continued)

(58) Field of Classification Search
CPC ........ F02B 63/047; F02B 77/08; F02D 29/06; F02D 41/22; G01N 33/004; G01V 8/12; H02P 9/08; H02P 2101/25
See application file for complete search history.

(56) References Cited

U.S. PATENT DOCUMENTS

2007/0085692 A1* 4/2007 Grant ..................... G08B 21/14
340/632
2017/0213468 A1* 7/2017 Duerksen ............... G08G 5/065
2018/0291822 A1 10/2018 Wischstadt et al.

FOREIGN PATENT DOCUMENTS

JP 2017166455 A * 9/2017
WO WO-2018/035434 A1 2/2018

OTHER PUBLICATIONS

Takamiya, JP 2017-166455, machine translation and partial human translation. (Year: 2017).*

* cited by examiner

*Primary Examiner* — Sizo B Vilakazi
*Assistant Examiner* — Mark L. Greene
(74) *Attorney, Agent, or Firm* — Foley & Lardner LLP (57) ABSTRACT

A generator including an internal combustion engine having an exhaust outlet, a proximity sensor structured to detect a distance value indicative of a distance between the exhaust outlet and an object, and a controller. The controller includes a proximity circuit structured to receive the distance value from the proximity sensor and a shutdown circuit. The shutdown circuit is structured to receive the distance value from the proximity circuit, determine whether to initiate at least one of an alarm and a shutdown of the generator based on the distance value and a predetermined distance value minimum, and initiate at least one of the alarm and the shutdown of the generator based on determining that the distance value is less than the predetermined distance value minimum.

21 Claims, 8 Drawing Sheets

(51) Int. Cl.
 *F02B 63/04* (2006.01)
 *G01V 8/12* (2006.01)
 *G01N 33/00* (2006.01)
 *F02B 77/08* (2006.01)
 *F02D 41/22* (2006.01)
 *H02P 101/25* (2016.01)
(52) U.S. Cl.
 CPC ............. *G01N 33/004* (2013.01); *G01V 8/12* (2013.01); *H02P 9/08* (2013.01); *H02P 2101/25* (2015.01)

PORTABLE GENERATOR INCLUDING PROXIMITY SENSOR

CROSS-REFERENCE TO RELATED PATENT APPLICATIONS

This application claims the benefit of U.S. Provisional Patent Application No. 62/730,352, filed Sep. 12, 2018, which is incorporated herein by reference in its entirety.

BACKGROUND

The present invention generally relates to internal combustion engines and generators powered by such engines. More specifically, the present invention relates to a carbon monoxide (CO) detection and shutdown system for a generator.

SUMMARY

One embodiment of the invention relates to a generator. The generator includes an internal combustion engine having an exhaust outlet, a proximity sensor structured to detect a distance value indicative of a distance between the exhaust outlet and an object, and a controller. The controller includes a proximity circuit structured to receive the distance value from the proximity sensor and a shutdown circuit. The shutdown circuit is structured to receive the distance value from the proximity circuit, determine whether to initiate at least one of an alarm and a shutdown of the generator based on the distance value and a predetermined distance value minimum, and initiate at least one of the alarm and the shutdown of the generator based on determining that the distance value is less than the predetermined distance value minimum.

Another embodiment of the invention relates to a shutdown controller unit. The unit includes a proximity sensor structured to detect a distance value indicative of a distance between the proximity sensor and an object and a controller. The controller includes a proximity circuit structured to receive the distance value from the proximity sensor and a shutdown circuit. The shutdown circuit is structured to receive the distance value from the proximity circuit, determine whether to initiate at least one of an alarm and a shutdown of a generator based on the distance value and a predetermined distance value minimum, and initiate at least one of the alarm and the shutdown of the generator based on determining that the distance value is less than the predetermined distance value minimum.

BRIEF DESCRIPTION OF THE DRAWINGS

The disclosure will become more fully understood from the following detailed description, taken in conjunction with the accompanying figures, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring generally to the figures, a generator shutdown controller or module is shown. Using input from various sensors, the shutdown controller determines the potential for an accumulation of carbon monoxide (CO) in the vicinity of the generator. The generator shutdown controller is thus configured to alert a user of the generator to the potential for CO accumulation in the vicinity of the generator. If the controller determines that the potential for CO accumulation continues during operation of the generator and the user has not yet shut down the generator, the generator may proceed to shut itself down. To determine the potential for CO accumulation, the shutdown controller can use sensors to detect the type of environment in which a generator is used. For example, the shutdown controller can receive inputs from sensors that detect the generator proximate a partially open garage door. In this type of environment, the exhaust gases from the generator have the potential to enter the enclosed space within the garage through the partially open door and accumulate within the enclosed space. The shutdown controller can detect this type of environment and alert the user to the potential for accumulation.

Figure 1:
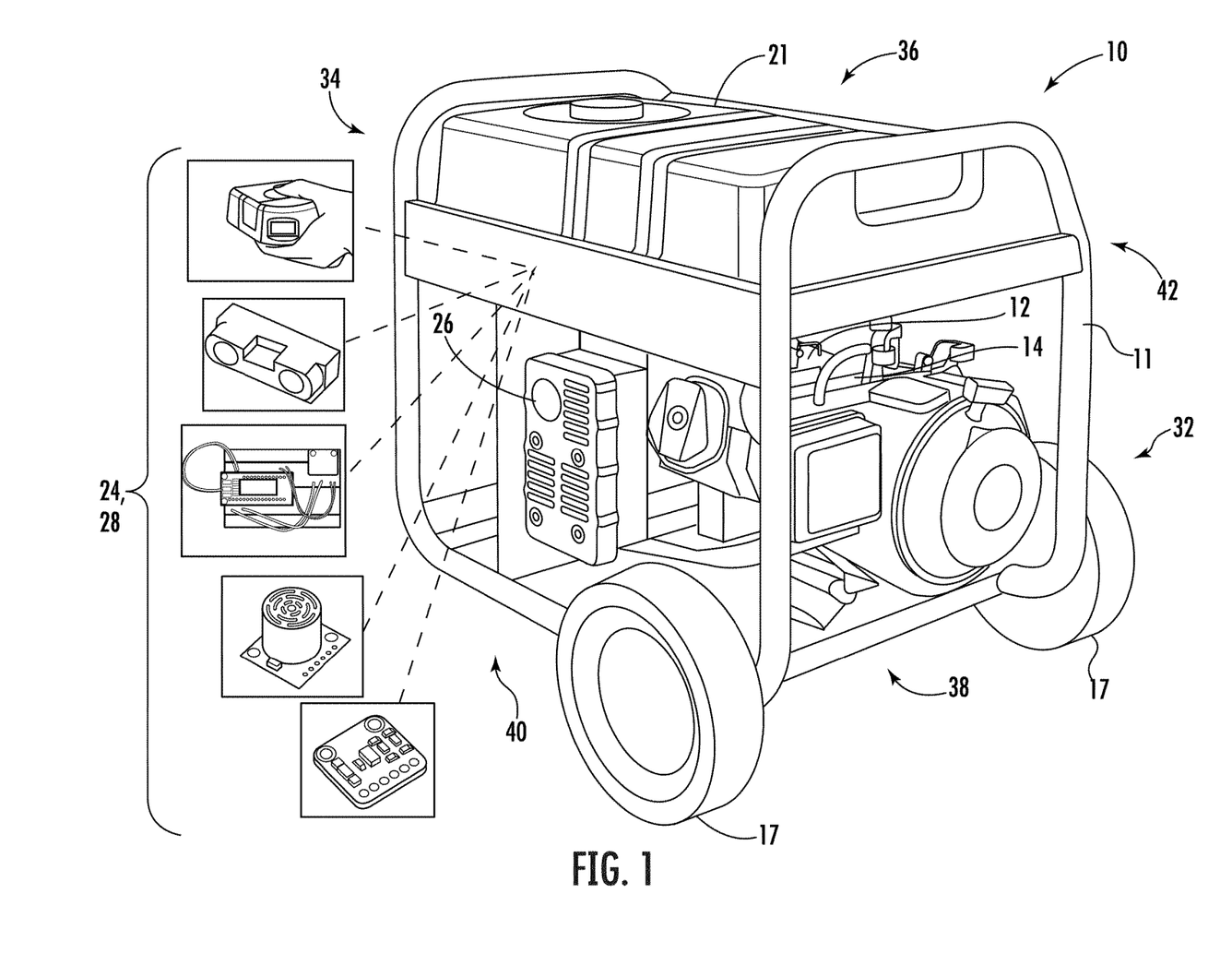
FIG. 1 is a perspective view of a generator according to an exemplary embodiment of the invention.
Figure 2:
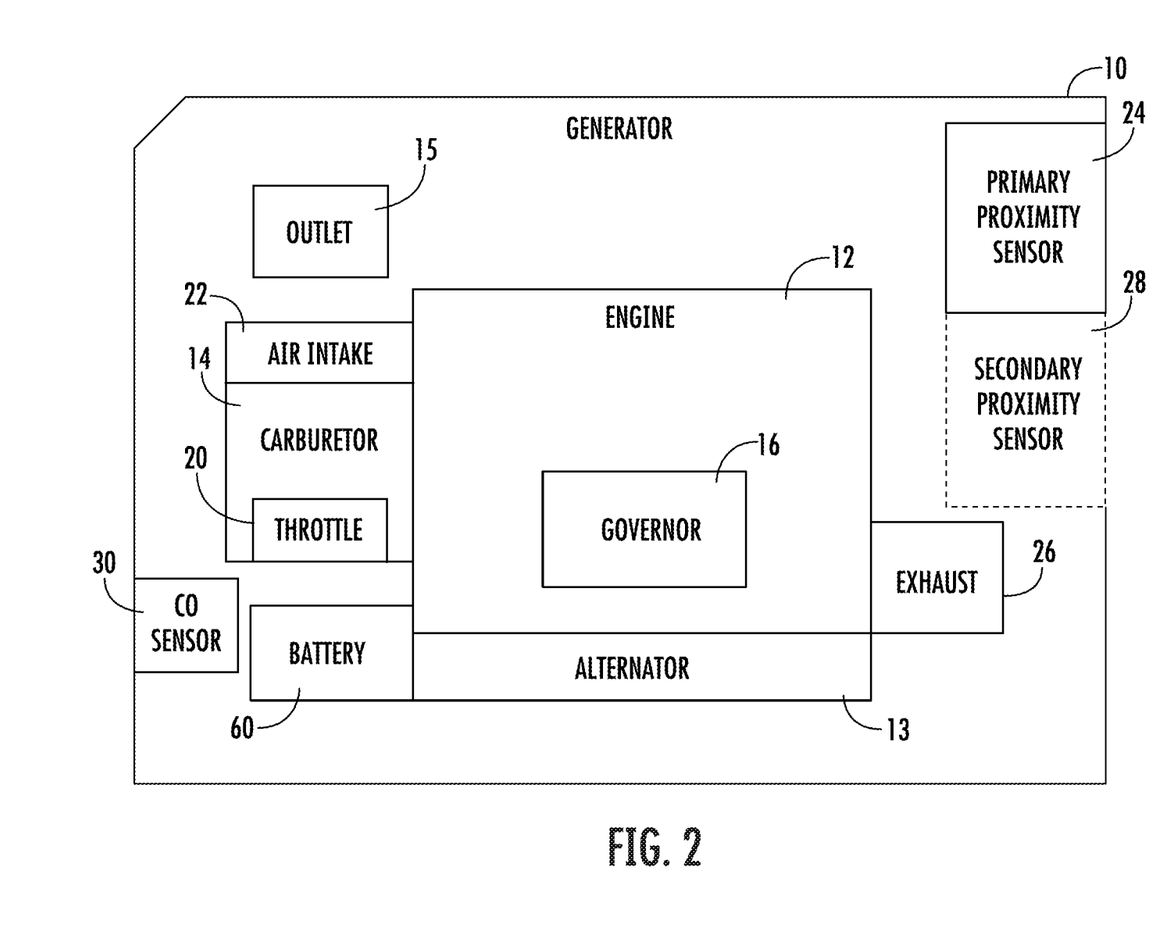
FIG. 2 is a schematic diagram of a generator according to an exemplary embodiment of the invention.

Referring to FIGS. 1-2, a generator is shown according to an exemplary embodiment. The generator 10 includes an engine 12, including a carburetor 14 or other air-fuel mixing device (e.g., electronic fuel injection, direct fuel injection, etc.), governor 16, throttle 20, air intake 22, exhaust outlet 26, and an alternator 13 driven by the engine 12. The alternator 13 produces electrical power from input mechanical power from the engine 12. The generator 10 additionally includes one or more outlets 15 for supply of the generated electrical power to an electrical device of a user's choosing. The generator 10 includes a front 32, rear 34, top 36, bottom 38, left side 40, and right side 42. The generator 10 can include one or more wheels 17 for portability and a frame 11 which supports one or more of the components of the generator 10. In some embodiments, a fuel tank 21 is positioned at the top of the generator 10 and supported by the frame 11 with the exhaust outlet 26 positioned below the fuel tank 21.

Air flows into the engine 12 from the air intake 22 and through the carburetor 14. As air passes through the carburetor 14, the air mixes with fuel entering the carburetor 14 from the fuel tank 21 and creates an air/fuel mixture that then enters the engine 12. The throttle 20 controls the flow of the air/fuel mixture that exits the carburetor 14. The governor 16 controls the position of the throttle 20 based on a detected load on the engine 12. The air/fuel mixture leaving the carburetor 14 is combusted in one or more cylinders of the engine 12 and exhaust gas from combustion leaves the engine 12 through the exhaust outlet 26. The exhaust gas is primarily made up of nitrogen, water vapor, and carbon dioxide, but a portion of the exhaust gas may be CO from incomplete combustion. Operation of a generator (or any other equipment powered by an engine) in a non-ventilated or insufficiently ventilated enclosed or partially enclosed space (e.g., volume), such as a garage, home, storage unit, pop-up tent, etc., can result in accumulation of CO within the space over time. In addition, in some cases where a generator is used near a partially enclosed space, such as a garage, exhaust gases can potentially enter the partially enclosed space through a partially-open door or window (e.g., a garage door), the accumulation of exhaust gases over time can result in an accumulation of CO within the space.

The various sensors and controllers described herein (e.g., shutdown controller 50, CO sensor 30, primary proximity sensor 24, secondary proximity sensor 28) may be used with other types of outdoor power equipment or portable jobsite equipment. Outdoor power equipment includes lawn mowers, riding tractors, snow throwers, pressure washers, portable generators, tillers, log splitters, zero-turn radius mowers, walk-behind mowers, riding mowers, industrial vehicles such as forklifts, utility vehicles, etc. Outdoor power equipment may, for example, use an internal combustion engine to drive an implement, such as a rotary blade of a lawn mower, a pump of a pressure washer, the auger of a snow thrower, the alternator of a generator, and/or a drivetrain of the outdoor power equipment. Portable jobsite equipment includes portable light towers, mobile industrial heaters, and portable light stands.

Referring to FIG. 2, the generator 10 includes a CO sensor 30 configured to detect the level or concentration of CO (e.g., parts per million (ppm)) proximate the generator 10. The CO sensor 30 communicates with the controller 50 described herein to alert a user to an elevated concentration of CO exceeding a predetermined threshold and also to control the shutdown of the generator 10 in these instances. In some embodiments, the CO sensor 30 includes a metal oxide gas sensor unit. The metal oxide gas sensor unit detects CO concentration via a gas sensitive film that is composed of tin or tungsten oxides. The sensitive film reacts with CO to determine CO concentration at the sensor unit. In other embodiments, the CO sensor 30 can include an electrochemical sensor. The electrochemical sensor measures the concentration of CO at the sensor by oxidizing or reducing the gases at an electrode and measuring the resulting current.

Figure 7:
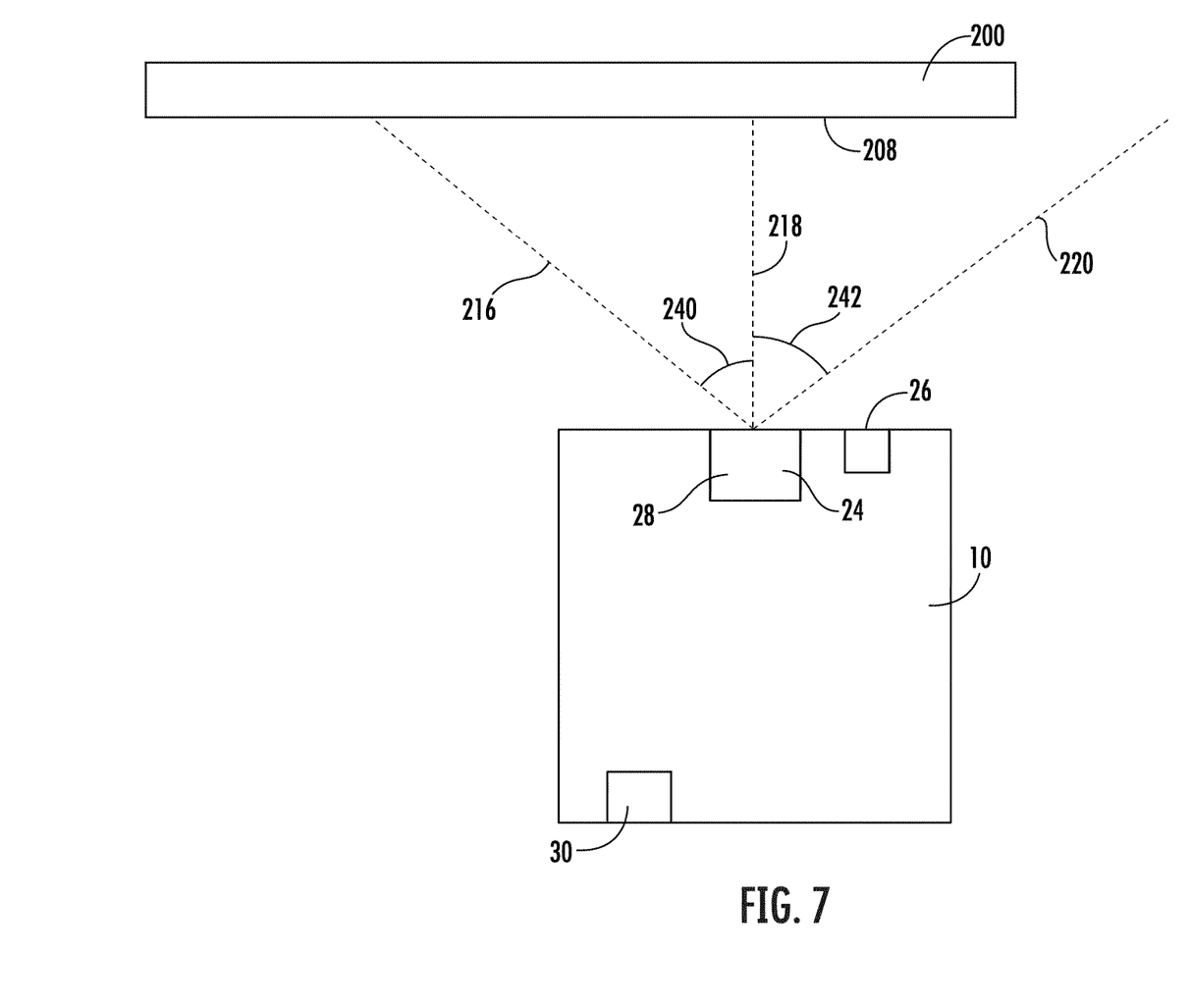
FIG. 7 is a diagram of the generator of FIGS. 1 and 2 operating in an outside environment proximate a structure, according to an exemplary embodiment of the invention.

Referring to FIGS. 1-2, the CO sensor 30 is positioned on the right side 42 near the front 32, while the exhaust outlet 26 is positioned on the left side 40 near the rear 34. In other embodiments, the CO sensor 30 may be positioned on another side of the generator 10 (e.g., front 32). While not limited to this exact positioning, the positioning of the CO sensor 30 may be selected such that exhaust gases exiting the exhaust outlet 26 are not blown back directly onto the CO sensor 30 in an environment with wind and/or air movement toward the exhaust outlet 26. Accordingly, when viewing the generator 10 from above (as shown in FIG. 7), the CO sensor 30 is positioned on an opposite side of the generator 10 from the exhaust outlet 26 (e.g., diagonally opposite, directly opposite). In some embodiments, when viewed from above, the CO sensor 30 is positioned on an opposite side of the generator 10 from the engine 12 with the engine 12 located between the sensor 30 and the exhaust outlet 26.

Still referring to FIG. 2, the generator 10 also includes one or more proximity sensors (e.g., shown as primary proximity sensor 24 and secondary proximity sensor 28) configured to determine the distance between the generator 10 and a nearby object or surface. The proximity sensors 24, 28 may also be configured to detect a person or animal proximate the generator 10 (e.g., using an infrared sensor) to differentiate a person or animal from a stationary surface or object. In various embodiments, the proximity sensors 24, 28 can include various types of sensors including, but not limited to, infrared sensors, ultrasonic sensors, acoustic sensors, lasers, or other types of sensors. As shown in FIG. 1, the primary proximity sensor 24 is positioned proximate the exhaust outlet 26 on the left side 40 of the generator 10 such that the shortest distance between the exhaust outlet 26 and a nearby surface or object can be determined. The secondary proximity sensor 28 and other potential proximity sensors are also positioned proximate the exhaust outlet 26 on the left side 40 of the generator 10. In other embodiments, the proximity sensors 24, 28 can be positioned on another side of the generator 10.

Figure 5:
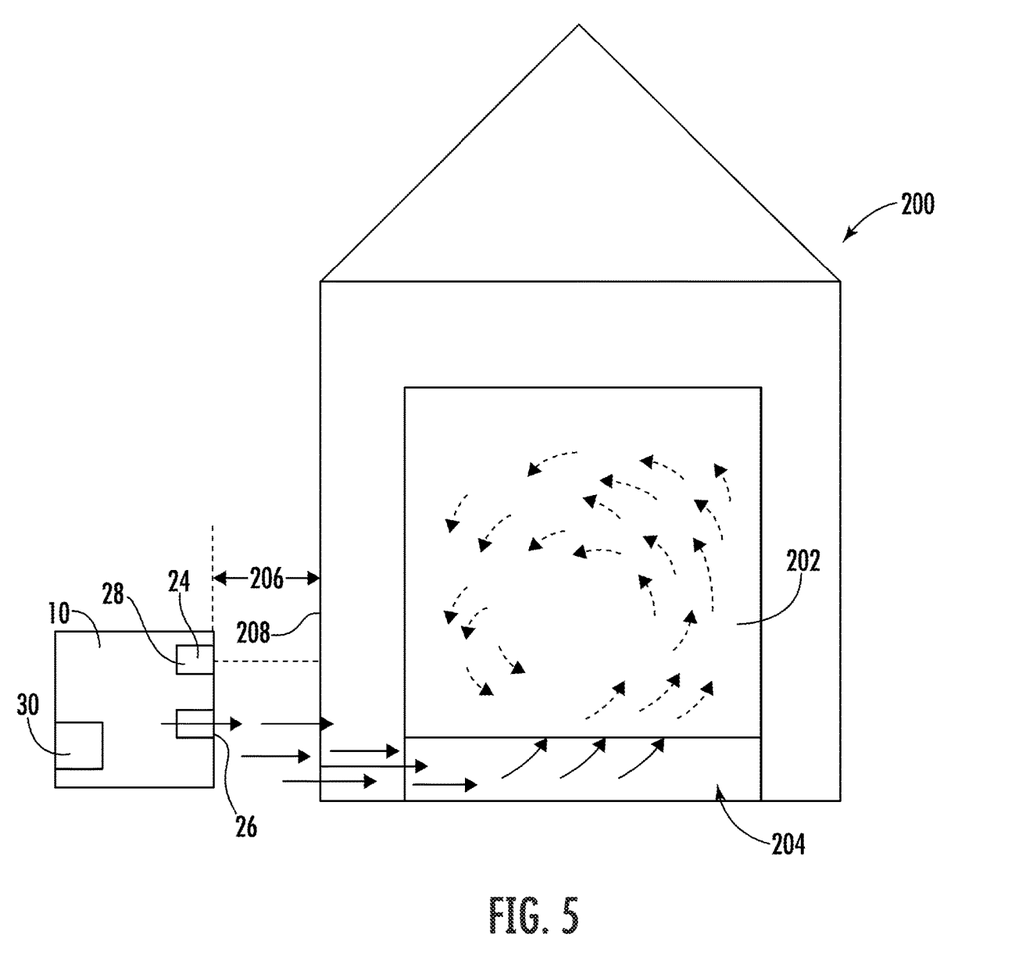
FIG. 5 is a diagram of the generator of FIGS. 1 and 2 operating in an outside environment proximate a structure, according to an exemplary embodiment of the invention.

Referring now to FIGS. 5-8, the generator 10 is shown in various environments. Referring to FIG. 5, the primary proximity sensor 24 is configured to determine the distance 206 between the generator 10 (e.g., the exhaust outlet 26) and a nearby object or surface 208 (e.g., garage door, side of building). For example, the generator 10 is positioned proximate a garage 200 and the distance 206 between the generator 10 and the nearest surface 208 of the garage 200 is determined. In some embodiments, a secondary proximity sensor 28 is used with the primary proximity sensor 24 to detect various characteristics of the environment in which the generator 10 is used.

Figure 6:
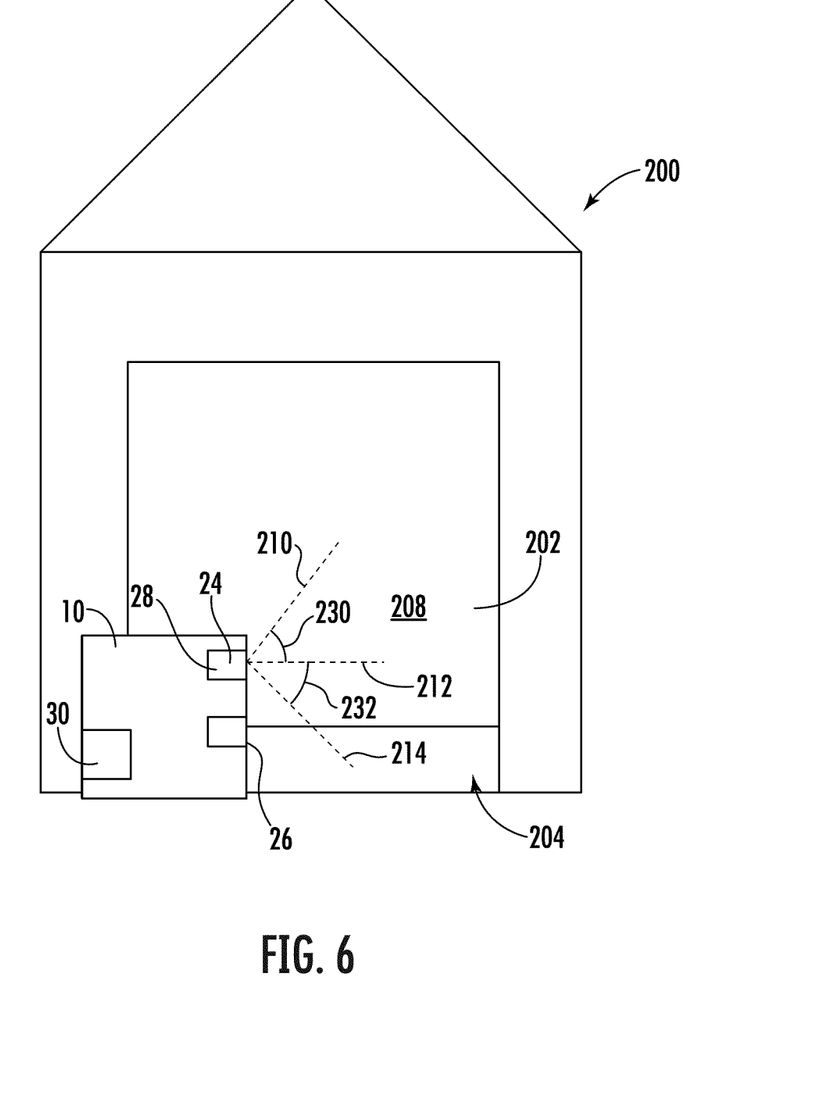
FIG. 6 is a diagram of the generator of FIGS. 1 and 2 operating in an outside environment proximate a structure, according to an exemplary embodiment of the invention.

Referring now to FIG. 6, in some embodiments, the secondary proximity sensor 28 can be used to determine the distance between the generator 10 and a nearby surface or object from a different vertical angle than that determined by the primary proximity sensor 24. Accordingly, the secondary proximity sensor 28 can be oriented such that the sensor 28 is pointed upward or downward relative to horizontal. In this way, the secondary proximity sensor 28 can be used to detect the presence and distance of objects proximate the generator 10 that are positioned at an angle upward or downward relative to horizontal. For example, as shown in FIG. 6, the primary proximity sensor 24 can be oriented such that a horizontal distance 212 (e.g., substantially perpendicular to the left side 40 of the generator 10) between the generator 10 and a nearby surface 208 is determined. The secondary proximity sensor 28 can be oriented such that a distance 210 between the generator 10 and a nearby surface 208 at an angle 230 above horizontal is determined. In addition, the secondary proximity sensor 28 (or a separate third proximity sensor) can be oriented such that a distance 214 between the generator 10 and a nearby surface 208 at an angle 232 below horizontal is determined. As such, objects or surfaces within a range above and below directly horizontal (e.g., ranging from an angle 232 below horizontal to an angle 230 above horizontal) from the generator 10 can be detected. As an example, as shown in FIG. 6, the sensors 24, 28 detect a surface 208 (e.g., a garage door) at horizontal and an angle 230 above horizontal, but at an angle 232 below horizontal no surface is detected. This determination can be used, as described further herein, to determine that an enclosure with a partially open portion 204, such as an opening in a garage door, is proximate the generator 10, and more specifically, proximate an exhaust outlet 26 of the generator 10. As shown in FIG. 5, in this type of environment, exhaust gases can exit the exhaust outlet 26 of the generator 10 and enter the partially open portion 204 below a partially open garage door 202 and accumulate within the enclosed space in the garage 200. By detecting the partially open portion 204 and the presence of a surface 208, the shutdown controller 50 can determine that a partially open enclosure is nearby and can trigger an alarm or shutdown of the generator 10.

In some embodiments, the secondary proximity sensor 28 can also be used to determine the distance between the generator 10 and a nearby surface or object from a different horizontal angle than that determined by the primary proximity sensor 24. Accordingly, the secondary proximity sensor 28 can be oriented such that the sensor 28 is pointed left or right of vertical. In this way, the secondary proximity sensor 28 can be used to detect the presence and distance of objects proximate the generator 10 that are positioned at an angle to the left or right relative to vertical. For example, as shown in FIG. 7, the primary proximity sensor 24 can be oriented such that a distance 218 (e.g., measured substantially perpendicular to the left side 40 of the generator 10) between the generator 10 and a nearby surface 208 is determined. The secondary proximity sensor 28 can be oriented such that a distance 216 between the generator 10 and a nearby surface 208 at an angle 240 to the left of measured distance 218 is determined. In addition, the secondary proximity sensor 28 (or a separate third proximity sensor) can be oriented such that a distance 220 between the generator 10 and a nearby surface 208 at an angle 242 to the right of measured distance 218 is determined. As such, objects or surfaces within a range to the left and right of distance 218 (e.g., ranging from angle 240 to the left to the angle 242 to the right) from the generator 10 can be detected. As an example, as shown in FIG. 7, the sensors 24, 28 detect a surface 208 at directly measured distance 218 and at an angle 240 to the left of distance 218, but at an angle 242 to the right of distance 218 no surface is detected. This determination can be used, as described further herein, to determine that an enclosure with a partially open surface, such as a door or window, is proximate the generator 10, and more specifically, proximate an exhaust outlet 26 of the generator 10.

In some embodiments, the secondary proximity sensor 28 can be used to determine the distance between the generator 10 and a nearby surface or object from a different horizontal angle and vertical angle than that determined by the primary proximity sensor 24 (e.g., a combination of FIGS. 6 and 7). In this way, if the secondary proximity sensor 28 detects both an object (e.g., a wall) on one side and an object (e.g., overhang, roof) overhead, the controller 50 can determine that the generator 10 is likely positioned in an alcove or semi-enclosed environment. In this case, as described further below, the controller 50 can shut down the generator 10 (e.g., via the shutdown circuit 54) or alert a user (e.g., via alert circuit 56 and notification 70).

Figure 8:
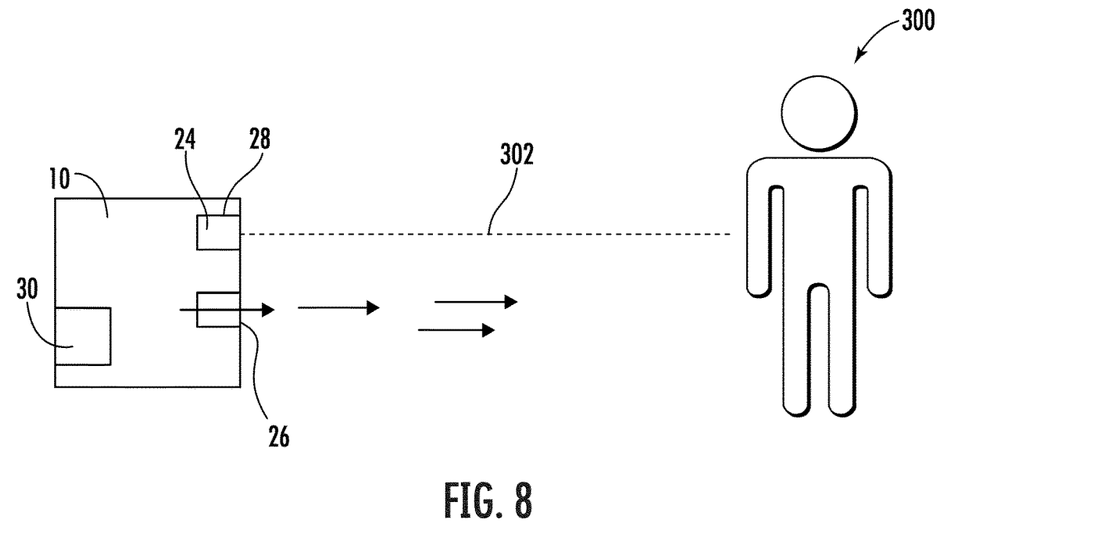
FIG. 8 is a diagram of the generator of FIGS. 1 and 2 operating in an outside environment proximate a person, according to an exemplary embodiment of the invention.

Referring now to FIG. 8, in some embodiments, the secondary proximity sensor 28 is configured to detect a heat signature 302 of an object 300 nearby the generator 10. The heat signature 302 is used to determine whether the object 300 detected is a surface of a building (or other non-living object) or a person or animal. The heat signature 302 of a person or animal is generally different from the heat signature of a building (e.g., person has higher heat signature), for example. The secondary proximity sensor 28 communicates the heat signature 302 to the shutdown controller 50 as described further herein. The heat signature 302 may be presented as a heat signature value (e.g., a binary value of 0 or 1) representing the difference between the heat signature of a person and the heat signature of a non-living object, such as a building. Using the differences in heat signature of non-living objects, such as the surface of a building, and the heat signature of living objects, such as people or animals, the controller 50 can protect against potential false tripping of a notification or alarm due to the detection of a passerby. In addition, as described further below, an analysis of the transience of detected nearby objects can be used to determine object permanence. Thus, objects that are merely fleeting in presence (e.g., a person or animal moving past the generator 10) can be filtered out of the shutdown or alert determination (e.g., made by the proximity circuit 52, shutdown circuit 54, alert circuit 56).

Referring back to FIG. 3, a schematic diagram of the shutdown controller 50 is illustrated, according to an exemplary embodiment. The various circuits of the shutdown controller 50, CO sensor 30, and proximity sensors 24, 28 may be included in a shutdown module (e.g., shown in FIG. 3 as the controller 50). Accordingly, the module can be separately attached to and removed from the generator 10 for use a separate unit. The shutdown controller is configured to control the operations of the CO sensor 30, including but not limited to, timing of generator shutdown and alerts, transmitting an alert to a user, triggering a visual alarm (e.g., indicator light), triggering an audible alarm (e.g., alarm bell), shutting down the generator, etc. As such, the shutdown controller 50 is communicably and operatively coupled to the CO sensor 30 and primary proximity sensor 24. In some embodiments, if a secondary proximity sensor 28 is included, the shutdown controller 50 is also communicably and operatively coupled to the secondary proximity sensor 28. To perform the functions described herein, the shutdown controller 50 includes a processing circuit, which includes a processor and a memory. The processor may be implemented as a general-purpose processor, an application specific integrated circuit (ASIC), one or more field programmable gate arrays (FPGAs), a digital signal processor (DSP), a group of processing components that may be distributed over various geographic locations or housed in a single location, or other suitable electronic processing components. The one or more memory devices (e.g., RAM, NVRAM, ROM, Flash Memory, hard disk storage) may store data and/or computer code for facilitating the various processes described herein. Moreover, the one or more memory devices may be or include tangible, non-transient volatile memory or non-volatile memory. Accordingly, the one or more memory devices may include database components, object code components, script components, or any other type of information structure for supporting the various activities and information structures described herein.

Figure 3:
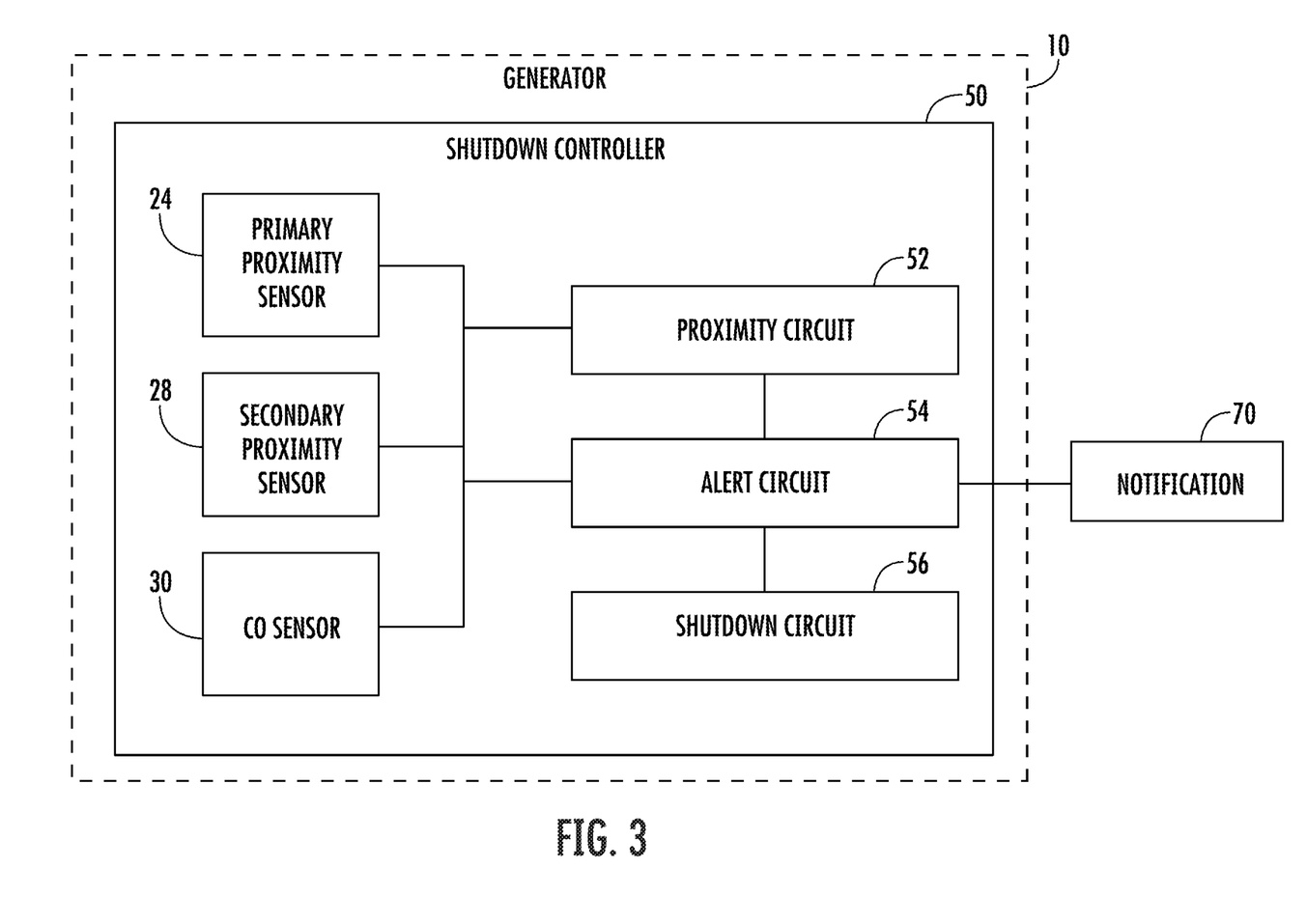
FIG. 3 is a schematic diagram of a shutdown controller of the generator of FIGS. 1 and 2, according to an exemplary embodiment of the invention.

The shutdown controller 50 includes a proximity circuit 52, a shutdown circuit 54, and an alert circuit 56, with all such circuits communicably coupled to each other. The proximity circuit 52 is configured to receive sensor output values from the primary and secondary proximity sensors 24, 28 (and any further proximity sensors used) relating to the detected generator environment (e.g., presence of nearby objects or surfaces, distance between generator and nearest objects or surfaces, etc.) and communicate the environment data to the shutdown circuit 54 and alert circuit 56. Accordingly, the proximity circuit 52 is communicably and operatively coupled to the shutdown circuit 54 and alert circuit 56 to provide the environment data. In some embodiments, the environment data may be provided in terms of distance values which are indicative of nearby surfaces or objects which may be indicative of nearby enclosures. In some embodiments, the environment data may also include an indication of the presence of people or animals that may be passing by the generator (e.g., heat signature data). The shutdown controller 50 may additionally include a database configured to store sensed CO values and environment data over time and corresponding response actions (e.g., generator shutdown, alert transmission, alert signal, self-diagnostics, etc.).

In addition, the proximity circuit 52 is further configured to perform an analysis of the transience of detected nearby objects, which can be used to determine the permanence status of detected objects, such as whether the object is stationary for a period of time or whether the object is moving past the generator 10. To determine the permanence status of an object, the proximity circuit 52 can use a time weighted value (e.g., transient value) applied to the distance of an object from the generator 10 as detected by the one or more proximity sensors 24, 28 over a period of time. The proximity circuit 52 determines the transient value of the object based on a difference between a first sensed distance value and a second sensed distance value over a predetermined period of time. If the proximity circuit 52 determines that the transient value is greater than a transient value threshold, the proximity circuit 52 can communicate with the shutdown circuit 54 and alert circuit 56 to disregard the object from a shutdown determination or an alert determination. As an example, if the distance of an object from the generator 10 is changing relatively quickly over a period of time (e.g., changes from twenty feet to five feet in five seconds), the proximity circuit 52 can use this information to determine that the object is likely moving past the generator 10. On the other hand, if the distance of an object from the generator 10 is changing relatively slowly or not changing at all, the proximity circuit 52 can use this information to determine that the object is likely stationary. Thus, objects that are merely fleeting in presence (e.g., a person or animal moving past the generator 10) can be filtered out of the shutdown or alert determination and objects that may be stationary can be considered as part of the shutdown or alert determination.

The shutdown circuit 54 is configured to receive the detected CO values from the CO sensor 30 and determine a value or concentration level of CO proximate the generator 10. Depending on indications of whether the generator 10 is in an open or enclosed space or near a partially-enclosed space using the environment data, the shutdown circuit 54 may treat sensed CO concentration data differently. To determine timing of an alert or a shutdown point of the generator 10, the shutdown circuit 54 may use a variety of methods. In some embodiments, the shutdown circuit 54 uses only environment data received from the proximity circuit 52 to determine timing of an alert or shutdown. In this case, if the generator 10 is positioned at a short enough distances from a detected surface or object, an alert or shutdown may be triggered regardless of the sensed CO level. Accordingly, the generator 10 is shut down or an alert is triggered based only on detection of objects in close proximity to the exhaust of the generator 10. In this way, if the generator 10 is positioned proximate potential combustibles, an alert or shut down is triggered regardless of the sensed CO level.

In some embodiments, the shutdown circuit 54 uses CO concentration data received from the CO sensor 30 combined with environment data received from the proximity sensors 24, 28 to determine timing of an alert or shutdown of the generator 10. For example, if a surface or object is detected at a short distance (e.g., three feet) from the generator 10, the predetermined sensed CO level threshold for a triggered shutdown or alert is much lower than if a surface or object is detected at a further away distance (e.g., thirty feet). Because CO typically accumulates quickly in an enclosed space environment, it is beneficial to be relatively sensitive to elevated CO concentrations in that environment to shut down the generator. The shutdown circuit 54 may additionally set an absolute maximum CO concentration threshold such that upon reaching the threshold, the generator 10 is shut down. Accordingly, at any point in time regardless of the environment in which the generator 10 is positioned, when an absolute CO threshold concentration (e.g., >300 ppm of CO) is detected, the generator 10 is shut down.

In some embodiments, the shutdown circuit 54 receives an indication that a detected object is a person or animal, the shutdown circuit 54 will also factor that detection into the shutdown or alert determination. Accordingly, if a person or animal is detected instead of a surface or object, the shutdown circuit 54 may determine that the generator 10 is not in an enclosed space or proximate a partially-enclosed space such that when a person or animal is detected, a shutdown or alert is not triggered. The shutdown circuit 54 may monitor the position of the person or animal and may trigger a shutdown if the person or animal has not moved for a set period of time.

The shutdown circuit 54 can also use elapsed runtime of the generator 10 to factor into the timing of an alert or shutdown. Accordingly, a timing circuit may be included with the generator 10 to determine the amount of time the generator 10 has been running. To determine run time, electrical output from the generator, spark plug data, and/or electric starter data may be used to determine the start of the generator operation, the duration of generator operation, the number of engine starting or stopping events within a certain period of time, etc. Additionally, calculations may be reset due to a sensed movement of the generator 10. Movement of the generator 10 can be sensed via a piezoelectric sensor positioned on the generator 10 configured to measure acceleration data.

Using the combination of generator environment and sensed CO levels (ppm), the controller 50 is configured to best guard against CO accumulations during potential enclosed or partially enclosed space running, while minimizing nuisance shutdowns. For example, if no surfaces or objects are detected near the generator 10 by the proximity sensors 24, 28, this may indicate that the generator 10 is located in an open air environment or an environment that is ventilated on at least one side. During open air running, air movement surrounding the generator 10 may cause exhaust gases to blowback onto the CO sensor 30 and cause false tripping of an alert or shutdown. When detecting that the generator 10 is in an open air or sufficiently ventilated environment, the level of CO that may trigger an alert or shutdown may be higher than the level of CO that would trigger an alert or shutdown when an object or surface is detected by the proximity sensors 24, 28. Accordingly, by determining the type of environment in which the generator 10 is positioned, the occurrence of nuisance shutdowns may be less frequent.

Once the shutdown circuit 54 has determined whether surfaces or objects are detected by the proximity sensors 24, 28, the shutdown circuit 54 triggers shutdown and/or alerts upon detection of a predetermined threshold for that type of environment. In this regard, the shutdown circuit 54 is coupled to an engine shutdown circuit of the engine 12 to complete a shutdown procedure. The shutdown procedure may include grounding the generator ignition for a period of time (e.g., ten seconds) until the engine 12 is turned off. The shutdown circuit 54 is also communicably and operatively coupled to the alert circuit 56 to communicate an indication that a threshold level has been reached for an alert to be triggered. The alert may be paired with a shutdown of the generator 10 and/or a warning of potentially elevated CO concentration without shutting down the generator 10. Accordingly, the alert may include illuminating light-emitting diodes (LEDs) on the user interface of the generator 10 to indicate that the generator is being or has been shut down.

After the generator 10 has been shut down, the shutdown circuit 54 may further be configured to remain in an active mode, where the shutdown circuit 54 is actively monitoring and preventing restart of the generator 10, for a period of time (e.g., 15 minutes). Accordingly, if a user tries to restart the generator 10 during this time, the shutdown circuit 54 will prevent the starting of the generator 10 and effectively "lock-out" the user from using the generator 10 during that time. As such, a user is prevented from restarting the generator 10 and further accumulating CO during times when the generator has been shut down based on high sensed CO concentrations or certain environment data. In some embodiments, instead of locking out the user, the generator 10 may be allowed to restart briefly, but immediately shutdown if a CO level threshold or environmental trigger is detected again. This may be advantageous to power management (e.g., battery life) of the system.

The alert circuit 56 is configured to communicate with the shutdown circuit 54 and the proximity circuit 52 to receive an indication that the generator 10 has been shut down due to sensed CO accumulation or an indication of the generator positioned in an environment in which CO accumulation may occur. The alert circuit 56 is configured to trigger a notification 70 (e.g., alarm system) on the generator 10 including, but not limited to, an indicator light and an audible alarm. In this configuration, if the user is signaled that the shutdown is due to CO emissions build-up in a non-ventilated space, the user is less likely to try to start the generator back up. The alert circuit 56 may trigger varying levels or intensities of alarms corresponding to the sensed concentration of CO, with alarm severity increasing with the increasing CO concentration or environment detection (e.g., warning light, warning audible alarm and then shut down, etc.). In some embodiments, the alert system is powered by a separate power supply than the sensing element to prolong the shutdown capability of the system.

In some embodiments, the alert circuit 56 is configured to switch over a mechanical switch to an elevated CO concentration indication position when a shutdown of the generator 10 occurs due to the detection of accumulated CO. Accordingly, the user will be notified of the CO detection by the physical location of the switch even though the generator 10 has been shut down and no electrical (e.g., sound or light) indication may be present. In the case of a shutdown switch, before starting the generator 10 back up after a shutdown, the user must first physically move the switch from the elevated CO concentration indication position back to an operating position. In some embodiments, the generator 10 may additionally include tamper resistant sensors. Accordingly, a user cannot easily disconnect or circumvent the sensors described herein. For example, power and communication wires to and from the CO sensor 30 may be combined in a single wire harness.

In some embodiments, the alert circuit 56 is additionally configured to communicate with a mobile device to alert a user that the generator 10 has been shut down due to sensed CO accumulation or certain environment detection. Accordingly, the user may be alerted on the mobile device while the user is away from the generator 10 and can proceed with caution if re-entering an enclosed space.

One or more batteries are included to power the components of the CO sensor 30 and shutdown controller 50. In some embodiments, the batteries are lithium-ion coin cell batteries. In other embodiments, the batteries may use different battery chemistries and/or structural configurations. A battery 60 (shown in FIG. 2) is coupled to the CO sensor 30 and the shutdown controller 50 to provide power to the sensing, detection, and shutdown operations of the generator 10. The battery 60 continues to provide power to the CO sensor 30 even when the generator 10 is shut down. This way, the CO sensor 30 is still actively monitoring CO concentration (e.g., via pulse detection) when the generator 10 is not running. The continuous operation of the CO sensor 30 allows the continuous monitoring of CO concentration in the vicinity of the generator 10 (e.g., every three minutes) and prevents the CO sensor 30 from resetting the baseline CO reading to zero ppm upon turning off power from the generator to the CO sensor 30. Without continuous supply of power to the CO sensor 30 from the battery 60, the sensor 30 may normalize the CO reading to zero ppm upon receiving power (even in areas with CO present), and accordingly, the CO reading may be skewed if power is not continuously supplied to the CO sensor 30.

An auxiliary battery can also be coupled to the controller 50 to provide power to the auxiliary systems included with the controller 50, such as the alert circuit 56 and the CO notification 70 (e.g., alert light, audible alarm, sensor self-diagnostics, etc.). Like the sensor battery 60, the auxiliary battery may also provide continuous power to the auxiliary systems of the sensor 30. Accordingly, an alert may still be transmitted, sounded, lit, etc. and self-diagnostics are still performed when the generator 10 is off.

The CO sensor 30 and controller 50 are continuously running self-diagnostics. If a problem is detected, such as low sensor battery, low alert battery, missing sensor module, the sensor is shorted, the sensor electrolyte is dried out, the sensor has reached the end of its sensor life, etc., an alert notification is triggered (e.g., red LED is illuminated once every 10 seconds) and the ignition is grounded to shut down the generator 10. The sensor failure mode triggers a lock-out condition such that a user cannot restart the engine 12 until the CO sensor 30 and/or controller 50 is replaced. In some embodiments, instead of locking out the user, the generator 10 may be allowed to restart briefly, but immediately shutdown if a CO level threshold trigger is detected again.

Figure 4:
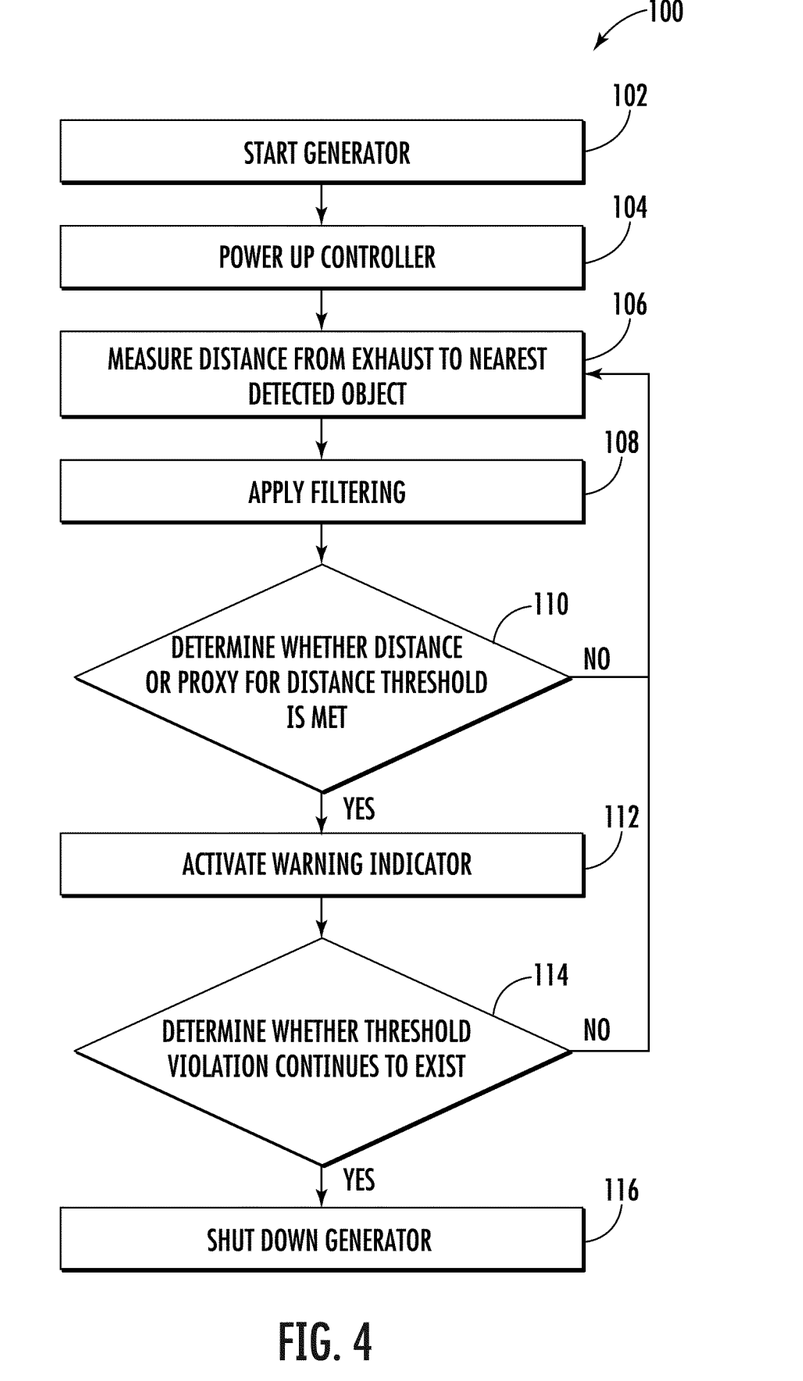
FIG. 4 is a method of operating the generator of FIGS. 1 and 2, according to an exemplary embodiment of the invention.

Referring to FIG. 4, a method for operating the generator is shown, according to an exemplary embodiment. The method 100 includes starting the generator 10 at 102 and powering up the shutdown controller 50 at 104. The distance between the generator 10 (e.g., the exhaust outlet 26) and the nearest detected object is measured at 106. The distance can be measured by one or more of the proximity sensors 24, 28. The proximity sensors 24, 28 are configured to determine the distance between the generator 10 and a nearby object or surface using sensors, which can include infrared sensors, ultrasonic sensors, acoustic sensors, lasers, or other types of sensors. The proximity sensors 24, 28 may also be configured to detect a person or animal proximate the generator 10 (e.g., using an infrared sensor) to differentiate a person or animal from a stationary surface or object. As shown in FIGS. 5-7, the proximity sensors 24, 28 are configured to determine the distance 206 between the generator 10 (e.g., the exhaust outlet 26) and a nearby object or surface 208 (e.g., garage door, side of building). For example, the generator 10 is positioned proximate a garage 200 and the distance 206 between the generator 10 and the nearest surface 208 of the garage 200 is determined. In some embodiments, a secondary proximity sensor 28 is used with the primary proximity sensor 24 to detect various characteristics of the environment in which the generator 10 is used.

Filtering is applied at 108. Various types of data filtering can be used. For example a trailing window average (TWA) of sensed CO concentration values can be calculated. In addition to monitoring the current CO concentration value, the shutdown circuit 54 can also calculate and monitor a trailing window average (TWA) of the sensed CO concentration values. As shown in the equation below, the TWA can be determined using the current CO concentration level, a prior loop value of TWA, and the number of loops over which the value is averaged.

$$TWA = TWA_{old}\left(\frac{n_{TWA} - 1}{n_{TWA}}\right) + ppm_{current\ reading}\left(\frac{1}{n_{TWA}}\right)$$

In the above equation, "$TWA_{old}$" is the prior loop value of the TWA, "$n_{TWA}$" is the number of loops over which the value is averaged, and "$ppm_{current\_reading}$" is the sensed CO concentration value.

At 110, it is determined whether the distance threshold or minimum is met. If the distance threshold or minimum is met, a warning indicator is activated at 112. If the distance threshold or minimum is not met, the process returns to 106, where the distance from the generator 10 to the nearest object is measured. For example, the distance threshold may include five feet or less such that if an object or surface is detected at five feet or less, a warning indicator is activated at 112. The warning indicator is controlled by the alert circuit 56, which is configured to trigger a notification 70 on the generator 10. The notification 70 can include, but is not limited to, an indicator light and an audible alarm. The alert circuit 56 may also trigger varying levels or intensities of alarms corresponding to the sensed distance violation or concentration of CO, with alarm severity increasing with the decreasing distances or increasing CO concentration (e.g., warning light, warning audible alarm and then shut down, etc.).

After a warning indicator is activated at 112, it is determined whether the distance threshold violation continues to exist at 114. If the distance threshold violation still exists, the process moves to 116, where the generator 10 is shut down. As described above, the shutdown procedure may include grounding the generator ignition for a period of time (e.g., ten seconds) until the engine 12 is turned off. The shutdown circuit 54 is also communicably and operatively coupled to the alert circuit 56 to communicate an indication that a threshold level has been reached for an alert to be triggered. The alert may be paired with a shutdown of the generator 10 and/or a warning of potentially elevated CO concentration without shutting down the generator 10. If the distance threshold violation does not still exist, the process moves to 106, where the distance from the generator 10 to the nearest object is measured and the monitoring process begins again.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

An exemplary system for implementing the overall system or portions of the embodiments might include a general purpose computing computers in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

What is claimed is:

1. A generator comprising:
   an internal combustion engine having an exhaust outlet; and
   a proximity sensor structured to detect a distance value indicative of a distance between the exhaust outlet and an object; and
   a controller comprising:
      a proximity circuit structured to receive the distance value from the proximity sensor; and
      a shutdown circuit structured to:
         receive the distance value from the proximity circuit;
         determine whether to initiate at least one of an alarm and a shutdown of the generator based on the distance value and a predetermined distance value minimum; and
         initiate at least one of the alarm and the shutdown of the generator based on determining that the distance value is less than the predetermined distance value minimum;
   wherein the distance value comprises a first distance value and the shutdown circuit is structured to initiate the alarm based on determining that the first distance value is less than the predetermined distance value minimum;
   wherein the shutdown circuit is further structured to receive a second distance value from the proximity circuit after activating the alarm and initiate the shutdown of the generator based on determining that the second distance value is less than the predetermined distance value minimum.

2. The generator of claim 1,
   wherein the shutdown circuit is further structured to deactivate the alarm based on determining that the second distance value is more than the predetermined distance value minimum.

3. The generator of claim 1, further comprising a carbon monoxide (CO) sensor, wherein the shutdown circuit is further structured to receive a detected level of CO from the CO sensor, determine whether to initiate at least one of the alarm and the shutdown of the generator based on the detected level of CO and a predetermined CO level threshold, and initiate at least one of the alarm and the shutdown of the generator based on determining that the detected level of CO is more than the predetermined CO level threshold.

4. The generator of claim 3, wherein the shutdown circuit is further structured to:
   determine whether to initiate the shutdown of the generator based on the detected level of CO, the second distance value, the predetermined distance value minimum, and the predetermined CO level threshold; and
   initiate the shutdown of the generator based on determining that the detected level of CO is more than the predetermined CO level threshold and the second distance value is less than the predetermined distance value minimum.

5. The generator of claim 1, wherein the controller further comprises an alert circuit structured to receive an indication from the shutdown circuit to trigger an alert on the generator; and trigger the alert on the generator.

6. The generator of claim 1, wherein the proximity sensor comprises a first proximity sensor and the generator further comprises a second proximity sensor;
   wherein the second proximity sensor is structured to determine a heat signature value of the object;
   wherein the shutdown circuit is structured to initiate at least one of the alarm and the shutdown of the generator based on the heat signature value and at least one of the first and second distance values.

7. The generator of claim 6, wherein the second proximity sensor includes an infrared sensor.

8. The generator of claim 1, wherein the proximity sensor comprises a first proximity sensor, and the generator further comprises a second proximity sensor structured to determine a third distance value measured at an angle relative to the first distance value;
   wherein the shutdown circuit is structured to initiate at least one of the alarm and the shutdown of the generator based on determining that the first distance value and the third distance value are less than the predetermined distance value minimum.

9. The generator of claim 1, wherein the proximity sensor includes at least one of an infrared sensor and an ultrasonic sensor.

10. The generator of claim 1, wherein the proximity sensor is further structured to determine the second distance value measured a predetermined period of time after the first distance value, wherein the controller is further structured to:
   determine a transient value of the object based on a difference between the first distance value and the second distance value over the predetermined period of time;
   determine that the transient value is greater than a transient value threshold; and
   disregard the object from a shutdown determination or an alert determination.

11. A shutdown controller unit comprising:
   a proximity sensor structured to detect a distance value indicative of a distance between the proximity sensor and an object; and
   a controller comprising:
      a proximity circuit structured to receive the distance value from the proximity sensor; and
      a shutdown circuit structured to:
         receive the distance value from the proximity circuit;
         determine whether to initiate at least one of an alarm and a shutdown of a generator based on the distance value and a predetermined distance value minimum; and initiate at least one of the alarm and the shutdown of the generator based on determining that the distance value is less than the predetermined distance value minimum;
wherein the distance value comprises a first distance value and the shutdown circuit is structured to initiate the alarm based on determining that the first distance value is less than the predetermined distance value minimum;
wherein the shutdown circuit is further structured to receive a second distance value from the proximity circuit after activating the alarm and initiate the shutdown of the generator based on determining that the second distance value is less than the predetermined distance value minimum.

12. The shutdown controller unit of claim 11, wherein the shutdown circuit is further structured to deactivate the alarm based on determining that the second distance value is more than the predetermined distance value minimum.

13. The shutdown controller unit of claim 11, further comprising a carbon monoxide (CO) sensor, wherein the shutdown circuit is further structured to receive a detected level of CO from the CO sensor, determine whether to initiate at least one of the alarm and the shutdown of the generator based on the detected level of CO and a predetermined CO level threshold, and initiate at least one of the alarm and the shutdown of the generator based on determining that the detected level of CO is more than the predetermined CO level threshold.

14. The shutdown controller unit of claim 13, wherein the shutdown circuit is further structured to:
determine whether to initiate the shutdown of the generator based on the detected level of CO, the second distance value, the predetermined distance value minimum, and the predetermined CO level threshold; and
initiate the shutdown of the generator based on determining that the detected level of CO is more than the predetermined CO level threshold and the second distance value is less than the predetermined distance value minimum.

15. The shutdown controller unit of claim 11, wherein the controller further comprises an alert circuit structured to receive an indication from the shutdown circuit to trigger an alert on the generator; and trigger the alert on the generator.

16. The shutdown controller unit of claim 11, wherein the proximity sensor comprises a first proximity sensor and the generator further comprises a second proximity sensor;
wherein the second proximity sensor is structured to determine a heat signature value of the object;
wherein the shutdown circuit is structured to initiate at least one of the alarm and the shutdown of the generator based on the heat signature value and at least one of the first and second distance values.

17. The shutdown controller unit of claim 16, wherein the second proximity sensor includes an infrared sensor.

18. The shutdown controller unit of claim 11, wherein the proximity sensor comprises a first proximity sensor, and the generator further comprises a second proximity sensor structured to determine a third distance value measured at an angle relative to the first distance value;
wherein the shutdown circuit is structured to initiate at least one of the alarm and the shutdown of the generator based on determining that the first distance value and the third distance value are less than the predetermined distance value minimum.

19. A generator comprising:
an internal combustion engine having an exhaust outlet;
a proximity sensor structured to detect a distance value indicative of a distance between the exhaust outlet and an object;
a carbon monoxide (CO) sensor; and a controller comprising:
a proximity circuit structured to receive the distance value from the proximity sensor; and
a shutdown circuit structured to:
receive the distance value from the proximity circuit;
determine whether to initiate at least one of an alarm and a shutdown of the generator based on the distance value and a predetermined distance value minimum; and
initiate at least one of the alarm and the shutdown of the generator based on determining that the distance value is less than the predetermined distance value minimum;
wherein the shutdown circuit is further structured to receive a detected level of CO from the CO sensor, determine whether to initiate at least one of the alarm and the shutdown of the generator based on the detected level of CO and a predetermined CO level threshold, and initiate at least one of the alarm and the shutdown of the generator based on determining that the detected level of CO is more than the predetermined CO level threshold;
wherein the shutdown circuit is further structured to:
determine whether to initiate the shutdown of the generator based on the detected level of CO, the distance value, the predetermined distance value minimum, and the predetermined CO level threshold; and
initiate the shutdown of the generator based on determining that the detected level of CO is more than the predetermined CO level threshold and the distance value is less than the predetermined distance value minimum.

20. A generator comprising:
an internal combustion engine having an exhaust outlet; and
a proximity sensor structured to detect a distance value indicative of a distance between the exhaust outlet and an object; and
a controller comprising:
a proximity circuit structured to receive the distance value from the proximity sensor; and
a shutdown circuit structured to:
receive the distance value from the proximity circuit;
determine whether to initiate at least one of an alarm and a shutdown of the generator based on the distance value and a predetermined distance value minimum; and
initiate at least one of the alarm and the shutdown of the generator based on determining that the distance value is less than the predetermined distance value minimum;
wherein the distance value comprises a first distance value and the shutdown circuit is structured to initiate the alarm based on determining that the first distance value is less than the predetermined distance value minimum;
wherein the shutdown circuit is further structured to receive a second distance value from the proximity circuit after activating the alarm and deactivate the alarm based on determining that the second distance value is more than the predetermined distance value minimum.

21. A shutdown controller unit comprising:
a proximity sensor structured to detect a distance value indicative of a distance between the proximity sensor and an object; and
a controller comprising:
   a proximity circuit structured to receive the distance value from the proximity sensor; and
   a shutdown circuit structured to:
      receive the distance value from the proximity circuit;
      determine whether to initiate at least one of an alarm and a shutdown of a generator based on the distance value and a predetermined distance value minimum; and
      initiate at least one of the alarm and the shutdown of the generator based on determining that the distance value is less than the predetermined distance value minimum;
wherein the distance value comprises a first distance value and the shutdown circuit is structured to initiate the alarm based on determining that the first distance value is less than the predetermined distance value minimum;
wherein the shutdown circuit is further structured to receive a second distance value from the proximity circuit after activating the alarm and deactivate the alarm based on determining that the second distance value is more than the predetermined distance value minimum.

* * * * *